(12) United States Patent
Adam et al.

(10) Patent No.: US 6,443,895 B1
(45) Date of Patent: Sep. 3, 2002

(54) WAVELET DEPULSING OF ULTRASOUND ECHO SEQUENCES

(75) Inventors: Dan Adam, Haifa; Oleg Michailovich, Technion, both of (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 09/948,596

(22) Filed: Sep. 10, 2001

Related U.S. Application Data

(63) Continuation-in-part of application No. PCT/US01/13590, filed on Apr. 27, 2001.
(60) Provisional application No. 60/231,538, filed on Sep. 11, 2000, and provisional application No. 60/203,510, filed on May 11, 2000.

(51) Int. Cl.[7] .................................................. A61B 8/00
(52) U.S. Cl. ........................................ 600/443; 73/602
(58) Field of Search ................................. 600/437, 443, 600/447; 73/602, 625–626; 342/145

(56) References Cited

U.S. PATENT DOCUMENTS

| | | | | |
|---|---|---|---|---|
| 4,063,549 A | * | 12/1977 | Beretsky et al. | 73/610 |
| 5,760,732 A | * | 6/1998 | Marmerelis et al. | 342/145 |
| 5,943,006 A | * | 8/1999 | Crane et al. | 342/196 |

* cited by examiner

Primary Examiner—Francis J. Jaworski
(74) Attorney, Agent, or Firm—Mark M. Friedman

(57) ABSTRACT

A method and an associated apparatus for imaging a target. An echo sequence image of the target is acquired and a log spectrum of at least a portion of the echo sequence image is computed. A low-resolution, shift-invariant wavelet projection of the echo sequence log spectrum is used as an estimate of the log spectrum of the point spread function. A frequency domain phase of the point spread function also is estimated. The relevant portion of the echo sequence image is deconvolved using the estimated point spread function.

11 Claims, 3 Drawing Sheets

WAVELET DEPULSING OF ULTRASOUND ECHO SEQUENCES

This is a continuation-in-part of PCT Application PCT/US01/13590, filed Apr. 27, 2001 and of U.S. Ser. No. 60/231,538 filed Sep. 11, 2000.

FIELD AND BACKGROUND OF THE INVENTION

The present invention relates to medical imaging and, more particularly, to a method of deconvolving an ultrasonic echo sequence, and to an ultrasound imaging apparatus that employs this method.

Because of the coherence of the back-scattered echo signals, images obtained from echo ultrasound imaging systems have extremely complex patterns that bear no obvious relationship to the macroscopic properties of the insonified object. The vast majority of biological tissues are extremely small on the scale of an acoustic wavelength. Consequently, a signal obtained within a resolution cell consists of contributions of many independent scatterers. Interference of these de-phased echoes gives rise to a pattern that has the appearance of a chaotic jumble of "speckles", known as speckle noise. The speckle pattern consists of a multitude of bright spots where the interference is highly constructive, dark spots where the interference is destructive, and brightness levels between these extremes. The presence of speckle noise in an ultrasound image reduces the ability of a user to resolve fine details. Speckle noise obscures very small structures, for example, early stage tumors, and decreases the reliability of tissue characterization. Therefore, the suppression of speckle noise is an important component of medical ultrasound imaging.

For the purpose of modeling the interaction of biological tissue with ultrasonic waves, the biological tissue is considered to be an assembly of reflectors and scatterers. A reflector is a plane interface that is large compared to the wavelength and that reflects portions of the transmitted energy back towards the transmitter. A scatterer is an object that is small compared to the wavelength and that scatters the transmitted signal in all directions. Such a system often is modeled as a (most generally 3D) function called the spatial response of insonified material, the reflectivity function, or (in medical applications) the spatial tissue response.

An ultrasound radio frequency (RF) image can be considered to consist of ID echo sequences, also known as "RF lines". Assuming the tissue properties to be uniform in the plane perpendicular to the scanning beam, an acquired 2D RF image can be viewed as the result of the convolution of the 2D reflectivity function (which accounts for inhomogeneity in the scanning plane) and the 2D transducer point spread function (PSF). Thus, the RF image can be considered to be a distorted version of the true reflectivity function, where the distorting kernel is the transducer PSF. This distortion includes the speckle noise discussed above.

In principle, it should be possible to measure the PSF in a calibration procedure, and then to deconvolve the PSF from the RF image. In practice, however, this is not possible, for several reasons. Perhaps the most important reason is that the absorption of ultrasound energy in tissues increases with frequency. This frequency-dependent attenuation causes both the PSF amplitude and the PSF shape to depend on depth in the tissue, leading to the observed non-stationarity of RF sequences.

In medical ultrasound, a pulse is transmitted into the tissue to be imaged, and the echoes that are backscattered to the emitting transducer are detected as a voltage trace RF line. The RF line conventionally is modeled as being a convolution of a hypothetical 1D PSF with a hypothetical 1D tissue reflectivity function. Assuming that the scatterers on each image line are located on a uniform grid, a discretized version of the received signal can be written as:

$$rf[n]=f[n]*s[n]+\text{noise}[n] \qquad (1)$$

where n is a time index, rf[n] is the RF line, s[n] is the transmitted ultrasound PSF, f[n] is a reflectivity sequence corresponding to the reflectivity function, noise[n] is measurement noise, and "*" represents convolution. Because the frequency-dependent attenuation process appears as a decrease with distance of the mean frequency and amplitude of the PSF, it is commonly assumed that the received echo signal may be expressed as a depth-dependent PSF convolved with the tissue reflectivity function. To make the PSF "location dependent", s[n] in equation (1) is replaced by s[n,k], where k is the location index. This leads to the observed non-stationarity of the RF lines received from the tissue. In order to deal with this non-stationarity, the RF-sequence is broken up into a number of possibly overlapping segments, such that within each segment the frequency-dependent attenuation process can be ignored and equation (1) holds. The problem of tissue characterization is thus reduced to a set of blind deconvolution problems: for each segment of a given RF line, the respective ultrasonic PSF should be estimated and used as described below.

To this end, homomorphic signal processing has been applied to rf[n]. Ignoring the noise term on the right hand side of equation (1) for now, transforming equation (1) to the frequency domain gives:

$$RF(w)=F(w)S(w) \qquad (2)$$

i.e., in the frequency domain, the frequency spectrum F(w) of the reflectivity sequence is multiplied by the frequency spectrum S(w) of the PSF to give the requency spectrum RF(w) of the echo sequence. These spectra can be written as $$RF(w)=|RF(w)|e^{j\cdot \arg(RF(w))} \qquad (3)$$

$$F(w)=|F(w)|e^{j\cdot \arg(F(w))} \qquad (4)$$

$$S(w)=|S(w)|e^{j\cdot \arg(S(w))} \qquad (5)$$

Taking the complex logarithm of both sides of equation (2) then gives $$\log|RF(w)|=\log|F(w)|+\log|S(w)| \qquad (6)$$

$$\arg[RF(w)]=\arg[A(w)]+\arg[S(w)] \qquad (7)$$

As described in the Annex, the log spectrum of the echo sequence, log |RF(w)|, thus is a sum of a smooth and regular log spectrum, log |S(w)|, of the PSF and a jagged and irregular log spectrum, log |F(w)|, of the reflectivity sequence. Cepstrum-based techniques have been used to exploit the qualitatively different natures of the PSF and reflectivity log spectra to isolate the PSF log spectrum for the purpose of estimating the PSF and deconvolving the estimated PSF from the echo sequence. See, for example, Torfinn Taxt, "Restoration of medical ultrasound images using two-dimensional homomorphic deconvolution", *IEEE Transactions on Ultrasonics, Ferroelectrics and Frequency Control*, vol. 42 no. 4 pp. 543–554 (July 1995); Torfinn Taxt, "Comparison of cepstrun-based methods for radial blind deconvolution of ultrasound images", *IEEE Transactions on Ultrasonics, Ferroelectrics and Frequency Control*, vol. 44 no. 3 pp. 666–674 (May 1997); J. A. Jensen and S. Leeman, "Nonparametric estimation of ultrasound pulses", *IEEE Transactions on Biomedical Engineering,* vol. 41 pp. 929 . 936 (1994); and J. A. Jensen, "Deconvolution of ultrasound images", *Ultrasonic Imaging,* vol. 14 pp. 1–15 (1992). Cepstrum-based techniques, however, suffer from certain limitations. Briefly, the complex cepstrum of a signal of finite duration has been shown to extend to infinity. This invariably leads to aliasing errors when the Discrete Fourier Transform or a similar discrete numerical method is used to compute the cepstrum.

Adam. in PCT Application No. US01/13590, which is incorporated by reference for all purposes as if fully set forth herein, teaches two alternative methods for estimating the PSF of an echo sequence. Both methods are based on discrete wavelet transforms. The first method is based on a low-resolution wavelet projection of the log spectrum of the echo sequence. The second method is based on the "soft-thresholding de-noising" algorithm of David L. Donoho and his coworkers (see references in US01/13590), modified to account for the fact that the log spectrum of the reflectivity sequence is not normally distributed.

Although the methods of US01/13590 perform better than the Cepstrum-based methods, the methods of US01/13590 suffer from the lack of translational invariance of discrete wavelet transforms. David L. Donoho and Ronald R. Coifman, in "Translation-invariant denoising", Technical Report 475, Department of Statistics, Stanford University (May 1995), proposed overcoming this drawback, in the context of the "soft-thresholding de-noising algorithm", by averaging out the translational dependence, a modification that they refer to as "cycle-spinning". Translational invariance is achieved, however, at the expense of an additional computational burden which may be excessive in some applications.

There is thus a widely recognized need for, and it would be highly advantageous to have, a computationally efficient, translationally invariant method of estimating an ultrasound PSF that would overcome the disadvantages of presently known methods as described above.

SUMMARY OF THE INVENTION

The present invention is based on the realization that "cycle-spinning", or its equivalent, is as applicable to the first method of US 01/13590 as it is to the second method of US 01/13590. In particular, the present invention includes a numerically efficient algorithm for implementing a translationally invariant low-resolution wavelet projection of the log spectrum of the echo sequence.

According to the present invention there is provided a method of imaging a target, including the steps of: (a) acquiring an echo sequence image of the target; (b) computing a log spectrum of at least a portion of the echo sequence image; (c) computing a low-resolution shift-invariant wavelet projection of the log spectrum; (d) estimating a point spread function from the low-resolution wavelet projection; and (e) deconvolving the at least portion of the echo sequence image with the point spread function.

According to the present invention there is provided an apparatus for imaging a target, including: (a) a transducer for acquiring an echo sequence image of the target; and (b) a processor for: (i) computing a log spectrum of at least a portion of the echo sequence image, (ii) computing a low-resolution shift-invariant wavelet projection of the log spectrum, (iii) estimating a point spread function from the low-resolution wavelet projection, and (iv) deconvolving the at least portion of the echo sequence image with the point spread function.

According to the method of the present invention, an echo sequence image of the target is acquired. As understood herein, an echo sequence image is a set of RF lines, acquired in parallel, from which the final video image of the target is to be calculated. Optionally, the echo sequence image is partitioned into a plurality of segments that may be either disjoint or overlapping. Subsequent processing is applied either to the echo sequence image as a whole or to one or more of the segments separately. This processing begins with the computation of the log spectrum of the time series (the whole echo sequence or the segment thereof) being processed.

At this point, a low-resolution shift-invariant wavelet projection of the log spectrum is computed. Preferably, this wavelet projection is performed by convolving the log spectrum with the sequence $$v[k]=2^{-M}(\hat{h}_M[k]*h_M[k])$$

where k is a frequency sample index, M is a resolution level index, $h_M$ is a discretized scaling function at resolution level M, and $\hat{h}_M$ is the mirror image of $h_M$. Preferably, $h_M$ is based on a Coiflet wavelet, on a minimum-phase Daubechies wavelet or on a symmetric Daubechies wavelet. The resulting low-resolution shift-invariant wavelet projection is an estimate of log $|S(w)|$.

An estimate of the frequency domain phase arg[S(w)] of the PSF is obtained, preferably under the assumption that the PSF is a minimum phase sequence. Equation (5) now gives an estimate of S(w), which is inverse Fourier transformed to give an estimate of the PSF. Finally, the estimated PSF is deconvolved from the time series (the whole echo sequence or the segment thereof) being processed. Preferably, this deconvolution is performed using an approximate inverse. Alternatively, this deconvolution is performed using a Wiener filter.

An apparatus of the present invention includes a transducer for acquiring an echo sequence image of the target and a processor for processing the acquired echo sequence image according to the method of the present invention.

Although the present invention is illustrated herein with reference to its primary application to ultrasound imaging, it is to be understood that the scope of the present invention extends to any imaging modality based on receiving echoes of signals transmitted by an impulsive energy source to a target, and to which the principles of the present invention are germane (for example, seismic exploration).

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method, and an associated system, for acquiring an echo sequence image of a target using an impulsive source of energy, and then estimating and deconvolving the point spread function of the impulsive source. Specifically, the present invention can be used to acquire medical ultrasound images with reduced speckle noise.

The principles and operation of echo sequence image acquisition and processing according to the present invention may be better understood with reference to the drawings and the accompanying description.

Figure 1:
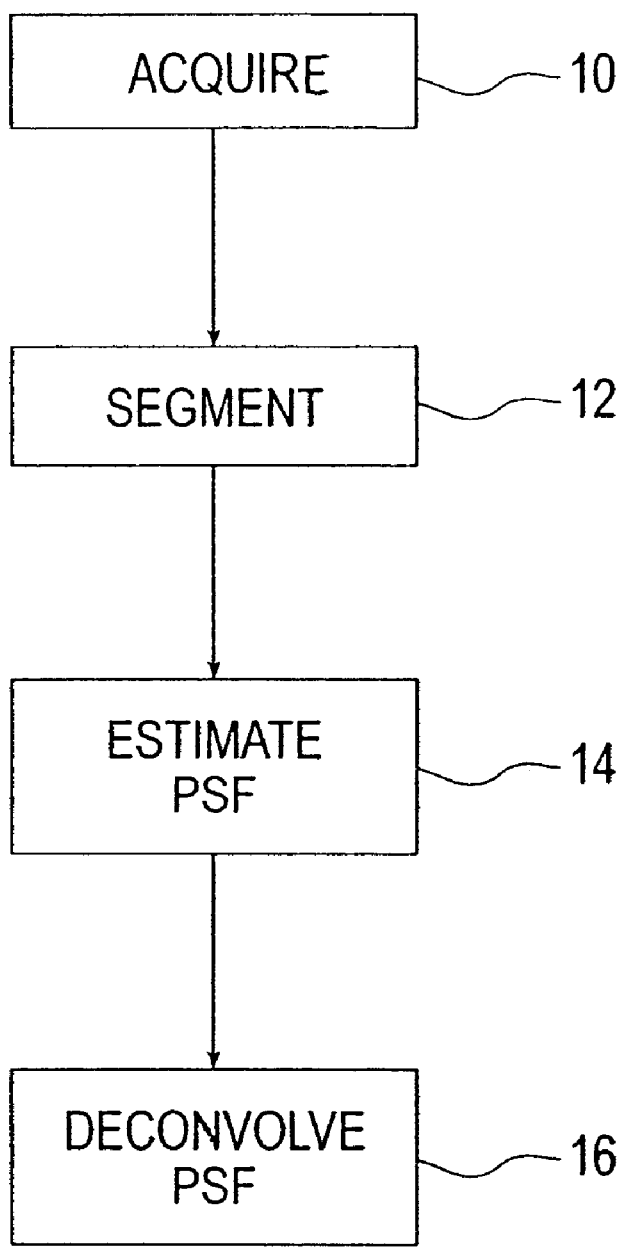
FIG. 1 is an overall flowchart of the methods of the present invention.

Referring now to the drawings, FIG. 1 is an overall flowchart of the method of the present invention.

In block 10, a 1D ultrasound echo sequence is acquired in the conventional manner.

In block 12, the acquired echo sequence is optionally partitioned into two or more subsequences. As described in Annex A of US 01/13590, biological tissue acts as a low pass acoustic filter, so that the frequency content of an ultrasound pulse decreases with time. To compensate for this effect, the echo sequence rf[n] usually is partitioned into a set of subsequences rf[n,k], such that, in each subsequence, the ultrasound PSF s[n,k] can be considered to have a well-defined frequency spectrum. The subsequences rf[n,k] may be either disjoint (i.e., nonoverlapping), or may overlap to a certain extent. In what follows, the subsequence index k will be suppressed for notational clarity.

In block 14, the PSF is estimated. The present invention, which is described in detail in the Annex, is a computationally efficient method for estimating the PSF. More precisely, the present invention is a computationally efficient method of estimating log $|S(w)|$. Specifically, a low-resolution shift-invariant wavelet projection of log $|RF(w)|$ is taken to represent log $|S(w)|$. arg[S(w)] is estimated as described below. Equation (5) then gives an estimate of S(w), whose inverse Fourier transform is the PSF.

In block 16, the estimated PSF is deconvolved from the echo sequence to give an estimate of the reflectivity sequence, as described below.

Figure 2:
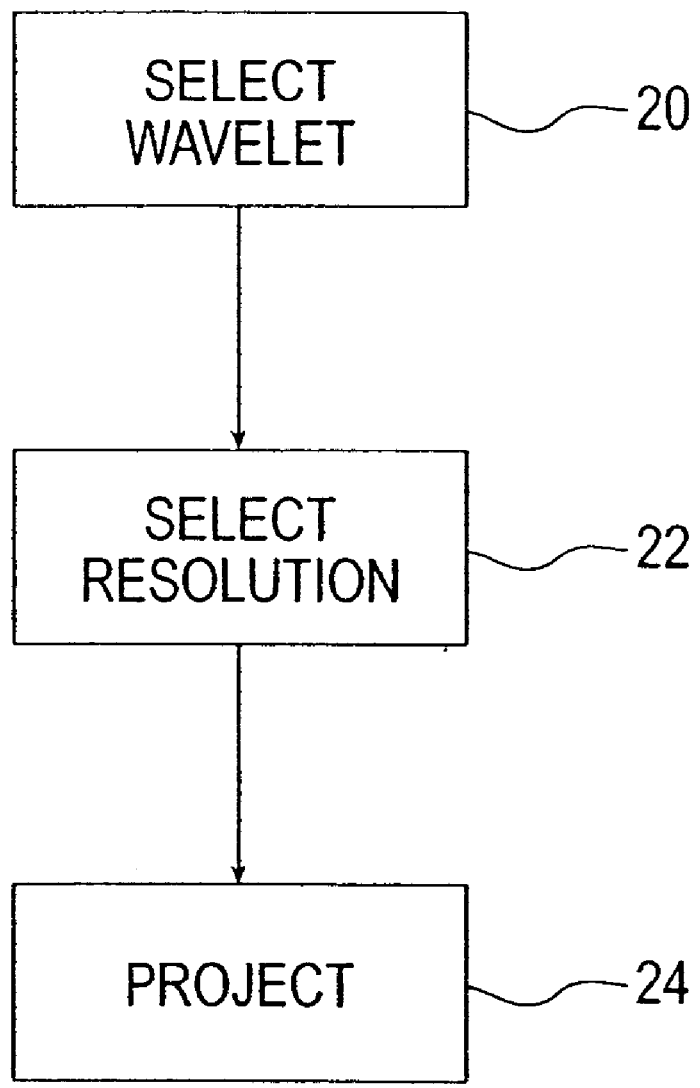
FIG. 2 is a flowchart of the low-resolution wavelet projection procedure.
Figure 3:
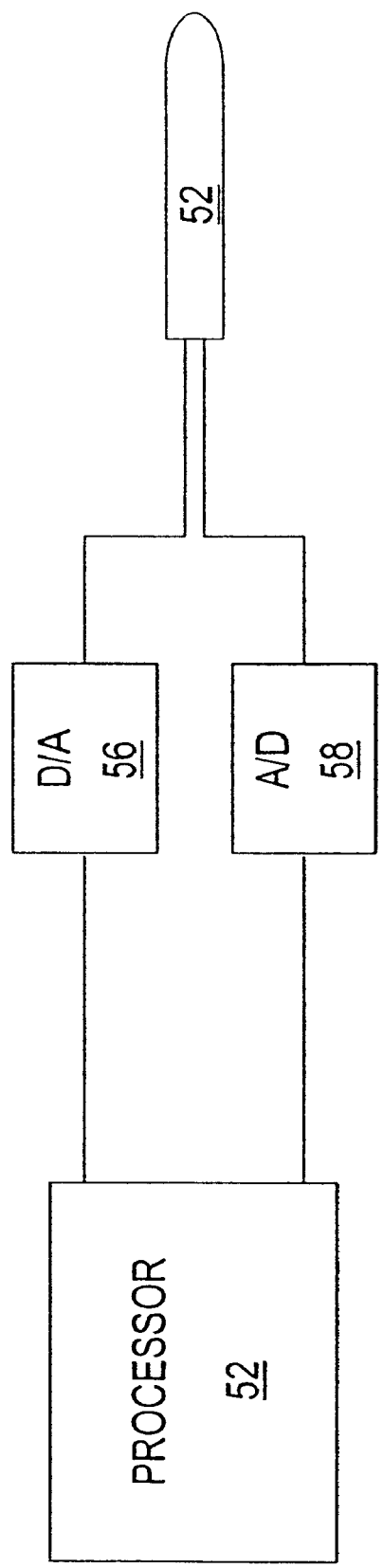
FIG. 3 is a high level block diagram of an ultrasound imaging apparatus of the present invention.

FIG. 2 is a flowchart of the low-resolution shift-invariant wavelet projection procedure.

In block 20, the wavelet function used in the wavelet decomposition of log $|RF(w)|$ is selected. Suitable wavelet functions include, among others, Coiflet wavelets, minimum-phase Daubechies wavelets and symmetric Daubechies wavelets, with minimum-phase Daubechies wavelets being preferred.

In block 22, the resolution level of the wavelet transform that distinguishes log $|F(w)|$ from log $|S(w)|$ is selected. One way of doing this is to calibrate the ultrasound probe by recording the pulse emitted by the probe, either directly or after reflection from a single planar reflector, treating this recorded pulse as a proxy for s[n], computing the corresponding log $|S(w)|$ and determining the number of wavelet coefficients needed to represent this proxy for log $|S(w)|$ with the desired degree of accuracy. As mentioned above, this measured proxy for s[n] can not be used directly for deconvolution of an acquired ultrasound echo sequence, for several reasons. First, the actual s[n] generally is low-pass filtered by the biological tissue. Second, the actual s[n] always differs from the proxy s[n] because of invariable variations in the conditions of acquisition, such as the degree of acoustical impedance mismatch between the ultrasound probe and the target. Nevertheless, the proxy of log $|S(w)|$ can be used to define the resolution level of the wavelet transform because the wavelet resolution levels needed to accurately represent the actual log $|S(w)|$ and the proxy of log $|S(w)|$ generally are identical.

The low-resolution wavelet projection itself is defined in equation (3.4) of the Annex. With a slight change of notation, this equation is:

$$\log|RF(n)| = \sum_{m=1}^{M} \sum_{k \in Z} c_{m,k} g_m[n - 2^m k] + \sum_{k \in Z} b_{M,k} h_M[n - 2^M k] \quad (8)$$

The second term on the right hand side of equation (8) is the low-resolution wavelet projection of log $|RF(w)|$ at resolution level M that is computed in block 24. The remainder of the right hand side of equation (8) is the high-resolution portion of log $|RF(w)|$. The second term on the right hand side of equation (8) is used in subsequent processing as an estimate of log $|S(w)|$.

$h_M[n]$ is the discretized version of the scaling function, at resolution level M, that is associated with the chosen wavelet function. As discussed in the Annex, the preferred way to compute the second term on the right side of equation (8) is to convolve log $|RF(w)|$ with the sequence $$v[k] = 2^{-M}(\hat{h}_M[k] * h_M[k]) \quad (9)$$

where $\hat{h}_M$ is the mirror-image of $h_M$, i.e., $h_M$ left-right reversed.

$|S(w)|$ having been estimated, arg[S(w)] now is estimated. As described in Annex A of US 01/13590, the preferred estimate of arg[S(w)] is a minimum phase estimate. If it is assumed that the PSF is a minimum phase sequence, then log $|S(w)|$ and arg[S(w)] are a Hilbert transform pair, so that an estimate of arg[S(w)] can be derived from the estimate of log $|S(w)|$.

With both $|S(w)|$ and arg[S(w)] now estimated, equation (5) gives an estimate of S(w). The inverse Fourier transform of this estimate of S(w) is an estimate of s[n], which is deconvolved from rf[n] by approximate inverse methods, as described, for example, in A. K. Louis, "Approximative inverse for linear and some nonlinear problems", *Inverse Problems*, vol. 11 no. 6 pp. 1211–1223 (1995). Alternatively, the estimate of s[n] is deconvolved from rf[n] using a Wiener filter.

What is claimed is:

1. A method of imaging a target, comprising the steps of:
    (a) acquiring an echo sequence image of the target;
    (b) computing a log spectrum of at least a portion of said echo sequence image;
    (c) computing a low-resolution shift-invariant wavelet projection of said log spectrum;
    (d) estimating a point spread function from said low-resolution wavelet projection; and
    (e) deconvolving said at least portion of said echo sequence image with said point spread function.

2. The method of claim 1, wherein said computing is effected by steps including convolving said log spectrum with a sequence $$v[k] = 2^{-M}(\hat{h}_M[k] * h_M[k])$$

wherein k is a sample index, M is a resolution level index, $h_M$ is a discretized scaling function at resolution level M, and $\hat{h}_M$ is a mirror image of $h_M$.

3. The method of claim 2, wherein $h_M$ is based on a wavelet function selected from the group consisting of Coiflet wavelets, minimum-phase Daubechies wavelets and symmetric Daubechies wavelets.

4. The method of claim 1, further comprising the step of:
    (f) partitioning the echo sequence image into a plurality of segments; said computing of said log spectrum, said computing of said wavelet projection, said estimating and said deconvolving then being effected separately for each said segment.

5. The method of claim 4, wherein said segments are disjoint.

6. The method of claim 4, wherein at least two of said segments at least partly overlap.

7. The method of claim 1, wherein said estimating of said point spread function includes estimating a frequency domain phase of said point spread function.

8. The method of claim 7, wherein said phase estimating assumes that said point spread function is a minimum phase sequence.

9. The method of claim 1, wherein said deconvolving is effected using an approximate inverse.

10. The method of claim 1, wherein said deconvolving is effected using a Wiener filter.

11. An apparatus for imaging a target, comprising:
(a) a transducer for acquiring an echo sequence image of the target; and
(b) a processor for:
  (i) computing a log spectrum of at least a portion of said echo sequence image,
  (ii) computing a low-resolution shift-invariant wavelet projection of said log spectrum,
  (iii) estimating a point spread function from said low-resolution wavelet projection, and
  (iv) deconvolving said at least portion of said echo sequence image with said point spread function.

\* \* \* \* \*